US00PP17580P3

(12) United States Plant Patent
Maillard et al.

(10) Patent No.: US PP17,580 P3
(45) Date of Patent: Apr. 10, 2007

(54) NECTARINE TREE NAMED 'NECTALADY'

(50) Latin Name: ***Prunus persica* var. *nucipersica***
Varietal Denomination: Nectalady

(75) Inventors: Laurence Maillard, Elne (FR); Arsene Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 11/115,221

(22) Filed: Apr. 27, 2005

(65) Prior Publication Data

US 2005/0241034 P1 Oct. 27, 2005

(30) Foreign Application Priority Data

Apr. 27, 2004 (QZ) ..... PRB 20040744

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP13,443 P2 * 12/2002 Gerdts et al. ..... Plt./190

OTHER PUBLICATIONS

Sales of nectarine trees for commercial planting in California, including graftings [online], [retrieved on Mar. 29, 2006]. Retrieved from the Internet <http://www.eatcaliforniafruit.com/ppn/growers–shippers/pdf/Nect_Tree_Sales_03.pdf> 4 pages.*

* cited by examiner

*Primary Examiner*—Kent Bell
*Assistant Examiner*—June Hwu
(74) *Attorney, Agent, or Firm*—Westerman, Hattori, Daniels & Adrian, LLP.

(57) ABSTRACT

A new and distinct variety of nectarine tree, denominated 'Nectalady', has fruit of very long shelf life without alteration after harvesting, a semi-sweet yellow flesh of high eating quality and an attractive, very high percentage red skin. The tree is of medium size and is vigorous. Moreover fruit can be consumed crunchy or at maturity.

4 Drawing Sheets

Latin name of the genus and species of the plant claimed: *Prunus persica* var. *nucipersica.*

Variety denomination: 'Nectalady'.

This application claims priority of Community plant variety right No. 2004-0744 filed on Apr. 27, 2004 which is hereby incorporated by reference in its entirety.

BACKGROUND OF THE NEW VARIETY

The present invention relates to a new and distinct variety of nectarine tree, *Prunus persica* var. *nucipersica*, which has been given the variety denomination 'Nectalady'. This new tree produces fruit with a long shelf life without alteration both on the tree after growth completion and after harvesting, very good eating quality, clingstone flesh fruit for fresh market in July in the Pyrénées-Orientales departement, France. Contrast is made to 'Maillarnecta' (Big Nectared®), 'Fairlane' and 'Maillarlate' nectarines, standard varieties, for reliable description. 'Nectalady' is a promising candidate for commercial success in that it has an early flowering, fruit with very long shelf life without alteration after harvesting, and so a very durable fruit.

ORIGIN OF THE VARIETY

'Nectalady' nectarine tree originated in a cultivated area of the south of France, in the Pyrénées-Orientales departement where it was tested. The variety results from an open pollinated cross of 'Maillarnecta' (Big Nectared®) yellow nectarine tree which was used as the seed parent. The pollen parent is unknown. 'Nectalady' was provisionally designated, tested and genetically identified by a genetic profile, as 01.24.93.02 NJ and is registered at the Official Catalogue of the Agriculture Ministry of the French Republic Dec. 17, 2003 under number 1014089. It was obtained by hybridizing and propagated by grafting. It has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant was reproduced asexually by us in Elne, Pyrénées-Orientales departement, France.

SUMMARY OF THE VARIETY

The new and distinct variety of nectarine tree blooms in early March at Perpignan in the Pyrénées-Orientales departement, France. More particularly, it blooms at the same time as 'Maillarnecta' (Big Nectared®), between $5^{th}$ and $20^{th}$ of March.

The first fruit of 'Nectalady' nectarine tree ripens early September, at the same time as the first fruit of 'Fairlane' variety. More particularly, it approximately ripens between September $1^{st}$ and $10^{th}$.

The first fruit of 'Nectalady' nectarine tree ripens 7 to 10 days after the first fruit of 'Maillarnecta' (Big Nectared®) variety. 'Nectalady' fruit size is medium instead of very big for 'Maillarnecta' (Big Nectared®) fruit. 'Nectalady' has a vivid red blush color on 90% to 100% of the fruit surface and a red-orange background, instead of a flat red blush color on 60% to 80% of the fruit surface and an orange background for 'Maillarnecta' (Big Nectared®) variety. The bloom quantity is more important for 'Nectalady' variety than for 'Maillarnecta' (Big Nectared®) variety.

DESCRIPTION OF THE DRAWINGS

In the accompanying drawing, which are as nearly true as it is reasonably possible to make in a color illustration of this type.

Figure 1:
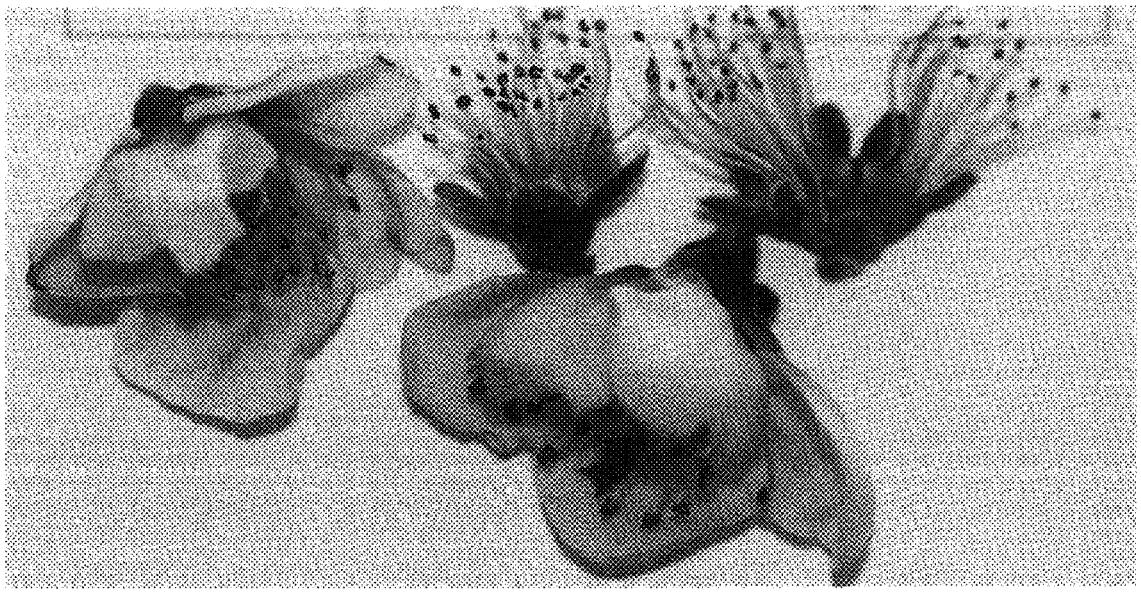
FIG. 1 is a color photograph which depicts the reverse and side view of the flower and the reproductive organs with petals removed of the new variety.
Figure 2:
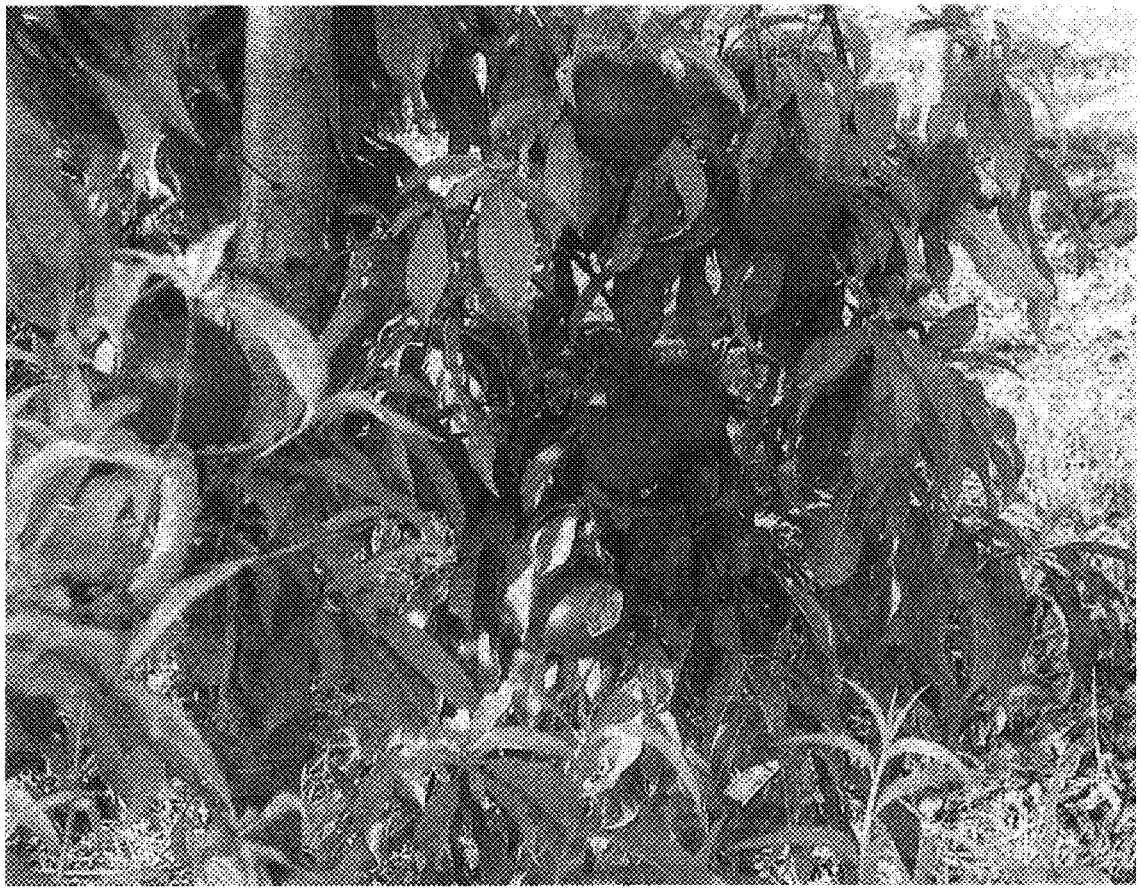
FIG. 2 is a color photograph which shows a typical specimen of the fruit, the leaf and branch of the new variety.
Figure 3:
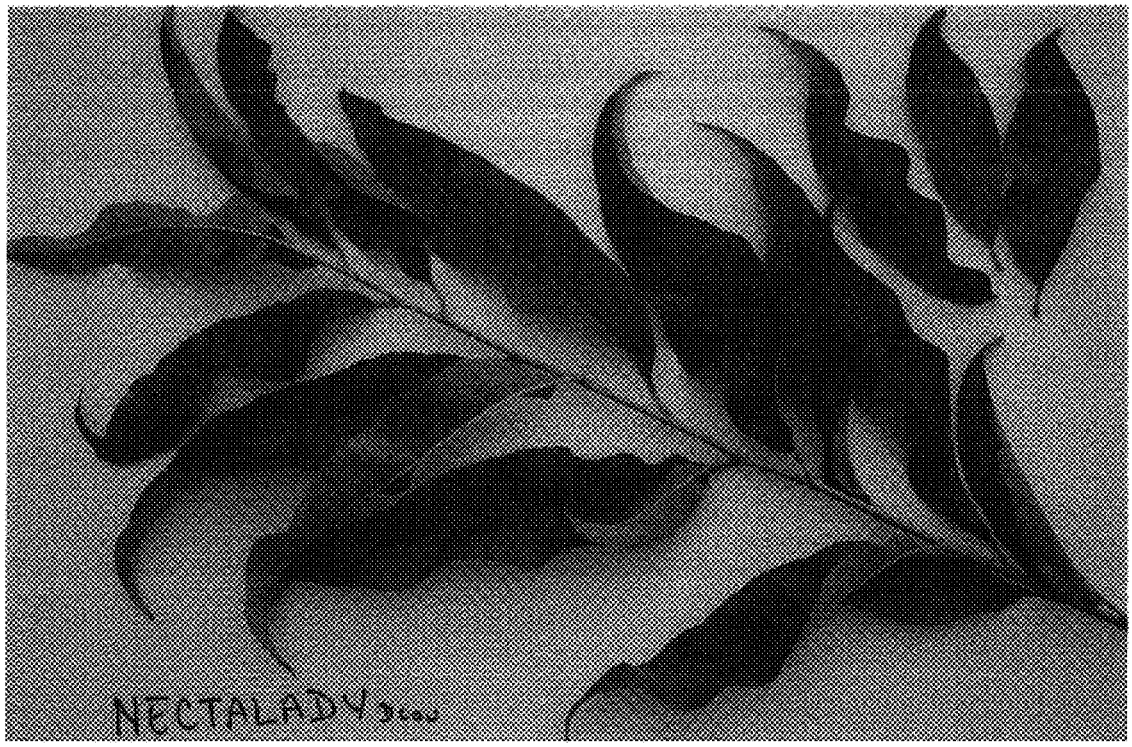
FIG. 3 is a color photograph which shows a twig bearing typical leaves and tree dorsal views of singles leaves of the new variety.
Figure 4:
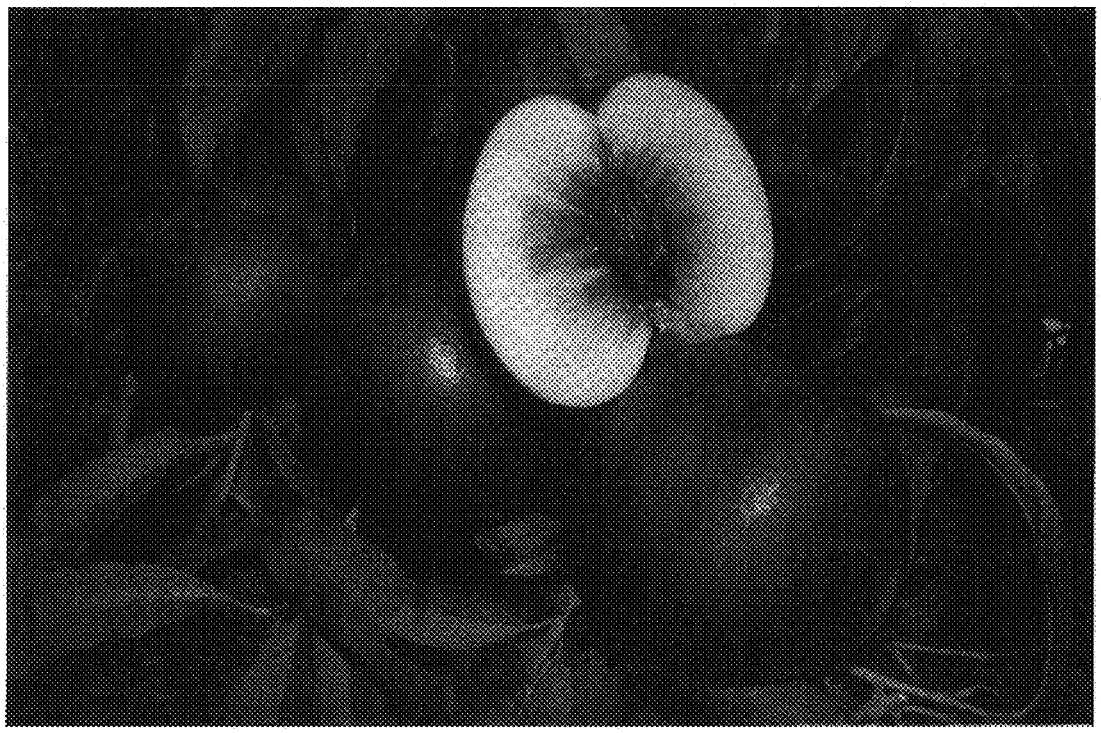
FIG. 4 is a color photograph which shows tree whole fruit, on their tree, sufficiently mature for harvesting and shipment; and a half-part of fruit which has been cut in half with the pit being left in the half-part, for depicting fruit flesh, pit cavity and stone of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'Nectalady' is high, due to fruit very long shelf life without alteration after harvesting.

Trees are vigorous and large stature half-standing in a semi-spread out aspect. The flowering shoot is present excluding brushwood side away from sun. Flowering begins early in springtime. The type of flower is showy with relative medium petal size. Petals are pale pink. Leaf glands are present and reniform. Time of maturity for consumption is late. The fruit flesh is yellow with a red pigmentation around the stone and its skin is very thick, very red with an orange-red background. The stone is medium size and the flesh is very adherent. Fruit taste semi-sweet.

Compared to 'Maillarlate' variety, 'Nectalady' has the same time of maturity although the red coloration is higher, 90% instead of 50%, and a semi-sweet taste instead of subacid. Shelf life of fruit is very long instead of being short.

Moreover fruit can be consumed crunchy or at maturity.

DETAILED DESCRIPTION

Referring more specifically to the pomological details of this new and distinct variety of nectarine tree, the following has been observed during the second fruiting season under the ecological conditions prevailing at the orchards located near the town of Elne, in the Pyrénées-Orientales departement, France. All observations have been made on rootstock cultivar. The rootstock was a 'Franc Inra Montclar®' tree. All major color code designations are by reference to The R.H.S. Color Chart (Fourth Edition) provided by The Royal Horticultural Society of Great Britain.

Tree:

Size:

*Generally.*—Considered medium large as compared to other common commercial nectarine cultivars. The tree size the first year was approximately 280 cm. The tree was pruned during each following dormant season to a height of approximately 250 cm. Current seasons shoots growth could reach 80 cm. So the tree size from the second year (second and next years) reached a final height of 330 cm with current seasons shots length comprised.

*Spread.*—Approximately 1.0 meter. The whole orchard was oriented to a central leader organisation, with tree lines spaced of 4.0 meters and trees spaced of 1 meter in a same tree line.

*Vigor.*—Considered vigorous. The present variety grew from about 200 cm to 280 cm in height during the first growing season. For second and following seasons, the variety was pruned to an approximate height of 250 cm.

*Productivity.*—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer.*—Very regular. A normal thinning was necessary for the tree valorisation. Thinning was necessary every year during the past 4 years.

*Form.*—The 'Nectalady' variety has naturally a semi-spread shape.

*Density.*—Considered medium dense and dense.

*Hardiness.*—The present tree was grown and evaluated in France. The variety appears to be hardy under typical central Pyrénées-Orientales departement climatic conditions. Experimentations on different sites with winter chilling requirement comprised between 350 hours and 1200 hours showed a good behaviour of the tree in all cases. No damages were caused by ascertained temperatures as low as −12 degrees Celsius. The tree was also very resistant to frosty springtime weather.

Trunk:

*Diameter.*—Approximately between 9.0 cm and 10.0 cm in diameter when measured at a distance of approximately 30 cm above the soil level, on trees from the second growing season. The branching begins at 50 cm above the soil level.

*Bark texture.*—Considered moderately rough, with numerous folds of papery scarfskin being present.

*Lenticels.*—Numerous lenticels are present on trees from the second growing season. The lenticels range in size from approximately 3.0 millimeters to 7.0 millimeters in width, and from 1.5 millimeters to 2.8 millimeters in height.

*Lenticel color.*—The outside of lenticels has a silver-grey color (RHS Grey 201 D to RHS Black 202 D), whereas the inside is considered brown (RHS Greyed Orange 166B).

*Bark coloration.*—The bark has a silver-grey color a little more pronounced than lenticels outside color (RHS Grey 201 C to RHS Black 202 C).

Branches:

*Size.*—Mature branches are considered medium to thick for the variety, and current season shoots are considered medium for the variety.

*Diameter.*—Average as compared to other nectarine varieties. The current season shoots have a diameter from 5.0 to 8.0 millimeters, and branches of trees from the second growing season have a diameter comprised between 25.0 and 35.0 millimeters.

*Surface texture.*—Average, wood which is several years old has no furrowed appearance.

*Crotch angles.*—Primary branches are considered variable, but the crotch angles are generally between 60 degrees and 70 degrees from the horizontal axis.

Current seasons shoots:

*Surface texture.*—Substantially glabrous.

*Internode length.*—Generally 25.0 millimeters to 32.0 millimeters.

*Color of mature branches.*—Medium brown (RHS Grey Brown 199 A).

Current season shoots:

*Color.*—The color of new shoot tips is considered a light yellow green (RHS Yellow Green 144 A-B) on lower part of new shoot tips, whereas the upper part is colored in brown-orange (RHS Greyed Orange 173 B-C-D).

Leaves:

*Size.*—Considered large for the species. Leaf measurements have been taken from vigorous, upright, current-season growth at approximately mid-shoot. The ratio leaf length/leaf width is above 4.

*Leaf length.*—Approximately 160.0 to 210.0 millimeters with leaf petiole.

*Leaf width.*—Approximately 40.0 to 50.0 millimeters.

*Leaf base shape.*—Slightly oblique relative to the leaf longitudinal axis.

*Leaf form.*—Lanceolate.

*Leaf tip form.*—Acuminate.

Leaf color:

*Upper leaf surface.*—Dark Green (RHS Green 137 A).

*Lower surface.*—Medium Green (RHS Green 137 B to 137 C).

*Leaf texture.*—Smooth and glabrous.

*Leaf venation.*—Pinnately veined.

Mid-vein:

*Color.*—Light yellow green (RHS Yellow Green 144 D to 144 C).

*Leaf margins.*—Slightly undulating.

*Form.*—Considered slightly denate.

*Uniformity.*—Leaves are isolated or grouped by 2 or 3. In this last case, it is found one leaf of normal size with one or two smaller leaves (size-reduction of 50% and more).

Leaf petioles:

*Size.*—Considered medium to long.

*Length.*—About 11.0 to about 15.0 mm.

*Diameter.*—About 2.0 to about 2.2 mm.

*Color.*—Light yellow green (RHS Yellow Green 144 D to 144 C).

Leaf glands:

*Size.*—Considered medium to large. Their length is about 1.5 millimeters.

*Number.*—Generally 4 glands.

*Type.*—Reniform.

*Color.*—On young leaves, leaf glands color is considered a pale green (RHS Green 144 B). On older leaves, leaf glands color turn to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

Flowers:

Flower buds:

*Generally.*—At pre-floral stage of development, the floral buds are conic in form with a round tip. Their form is evolving until blooming, with variables dimensions. Just before blooming, floral buds are approximately 10.0 millimeters wide and approximately 18.0 millimeters long.

Flower buds:

*Color.*—This characteristic is dependent upon the proximity to bloom. At pre-floral stage of development, the bottom of the flowers buds, formed by sepals, is of purple-brown color (RHS Greyed Purple 183 A); the corolla, formed by petals, is generally of pale pink color (RHS Red Purple 69 C). Petals color shows an evolution until the end of flowering. The buds are considered hardy under typical central Pyrénées-Orientales departement climatic conditions.

*Hardiness.*—No winter injury was noted during the last several years of evaluation in the central Pyrénées-Orientales departement, with winter temperatures as low as −12° C. in December or January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom.*—Generally March. The first bloom, observed on Feb. 24, 2002, was exceptionally early. Second and third blooms took place respectively on Mar. 9, 2003 and Mar. 5, 2004.

*Blooming time.*—Considered early-season in relative comparison to other commercial nectarine cultivars grown in the Pyrénées-Orientales departement, France. The date of full bloom is observed on March. The date of bloom varies slightly with climatic conditions and cultural practices. Thus the first full bloom was observed on Mar. 3, 2002, second full bloom on Mar. 17, 2003 and third full bloom on Mar. 13, 2004.

*Duration of bloom.*—Approximately 16 days. This characteristic varies slightly with the prevailing climatic conditions.

*Flower type.*—The variety is considered to have a showy type flower.

*Flower size.*—Considered medium. Flower diameter at full bloom is approximately 31.0 to 36.0 millimeters.

*Bloom quantity.*—Considered abundant, approximately 45 flowers per meter.

*Flower bud frequency.*—Generally 2 flower buds appear per node, occasionally 1.

Petal size:

*Generally.*—Considered medium for the species.

*Length.*—Generally about 19.0 millimeters.

*Width.*—Generally about 18.0 millimeters.

*Petal form.*—Round-shaped.

*Petal count.*—Nearly always 5.

*Petal texture.*—Smooth and glabrous.

*Petal color.*—Pale Pink (RHS Red Purple 69 C) when young, darkening with advancing senescence.

*Fragrance.*—Slight.

Petal claw:

*Form.*—The claw is considered to have a conic form with a slightly rounded extremity.

*Length.*—Approximately 8.0 to 10.0 millimeters.

*Width.*—Approximately 6.0 to 8.0 millimeters.

*Petal margins.*—Generally slightly undulated.

Petal apex:

*Generally.*—The petal apices are generally entire at the tip, and dome-shaped.

Flower pedicel:

*Length.*—Considered medium and having an average length of approximately 3.0 to 5.0 millimeters.

*Diameter.*—Considered average, approximately 2.0 millimeters.

*Color.*—A medium brown (RHS Grey Brown N199 B to C).

Flower nectaries:

*Color.*—A flat golden orange (approximately RHS Greyed Red 178 C-B).

Calyx:

*Internal surface texture.*—Smooth and glabrous.

*Color.*—The outer surface of the calyx is considered of Purple-brown (RHS Greyed Purple 183 A) color.

Sepals:

*Surface texture.*—The outer surface has a short, fine pubescent texture.

*Size.*—Average.

*Color.*—A flat Red (approximately RHS Greyed Red 178 A).

*Average number of stamens per flower.*—Approximately comprised between 80 and 100 stamens per flower.

Anthers:

*Generally.*—Average in length.

*Color.*—Red to orange-red color (approximately RHS Greyed Purple 178 A Group). Anthers are becoming yellow at maturity.

*Pollen production.*—Pollen is abundant, and has a yellow color (Approximately RHS Yellow Orange 17 B-C). The present variety is considered self fruitful (self-pollinating).

Filaments:

*Size.*—Variable in length, approximately 11.0 to 16.0 millimeters in length. In all cases filament's length is superior or equal to pistil's length.

*Color.*—Considered light pink (approximately RHS Red Purple 62 C-D).

Pistil:

*Number.*—Usually 1, rarely 2.

*Generally.*—Average in size.

*Length.*—Approximately 15.0 to 21.0 millimeters including the ovary; Smaller or equal to filament's length.

*Color.*—Considered a very pale green (varying from RHS Yellow Green 150 D Group to RHS Yellow Green 151 D Group).

*Surface texture.*—Glabrous.

Fruit:

*Maturity when described.*—Firm ripe condition (shipping ripe).

*Date of first picking.*—Sep. 1, 2003.

*Date of last picking.*—Sep. 10, 2003. The date of harvest varies slightly with the prevailing climatic conditions. The 'Nectalady' variety has a late date of picking, and a grouped maturity; only 3 harvests in 10 days were necessary.

Size:

*Generally.*—Considered large, with a homogeneous size between them.

*Average cheek diameter.*—Approximately 76.0 millimeters.

*Average axial diameter.*—Approximately 74.0 millimeters.

*Typical weight.*—Generally between 180.0 grams and 220.0 grams. This characteristic is high dependent upon the prevailing cultural practices, and therefore is not particularly distinctive of the variety.

Fruit form:

*Generally.*—Round to slightly oblate. The fruit is generally uniform in symmetry, viewed from pistil end.

*Fruit suture.*—Very shallow and smooth, extending from the base to the apex. No apparent callousing or stitching exists along the suture line.

Suture:

*Color.*—This has generally a color similar to the whole fruit color, a vivid red (RHS Red 53A) on a red-orange background (RHS Orange Red N 34 A).

Ventral surface:

*Form.*—Smooth.

*Apex.*—Non prominent, slightly depressed, very small.

*Base.*—Shallow.

*Stem cavity.*—Generally elongated in the suture plane. Average depth of the stem cavity is about 1.0 cm. Average width is about 2.0 cm.

Fruit skin:

*Thickness.*—Considered very thick and strong, and tenacious to moderately tenacious to the flesh depending on stage of maturity.

*Texture.*—Glabrous.

*Taste.*—Semi-sweet.

*Tendency to crack.*—None observed.

Color:

*Blush color.*—This blush color is an homogenous vivid red (RHS Red 53A). The red blush covers 90% to 100% of the fruit skin surface. The percentage of the blush on the fruit skin surface can vary, and is generally dependant upon the prevailing conditions under which the fruit was grown.

*Ground color.*—The ground color appears on 10% to 20% of the fruit skin surface, and is considered orange-red (RHS Orange Red N 34A).

*Fruit stem.*—Medium in length, approximately 12.0 millimeters.

*Diameter.*—Approximately 4.0 millimeters.

*Color.*—Pale green (RHS Yellow Green 145A to 145 B).

Flesh:

*Ripens.*—Very evenly, homogenous, slow.

*Texture.*—Very firm, very dense, juicy at harvest maturity stage.

*Fibers.*—Not fibrous.

*Aroma.*—Pronounced.

*Eating quality.*—Considered very good and spicy.

*Flavor.*—Considered semi-sweet. The Brix is elevated and acidity is comprised between 6 and 9 meq/100 ml, nearly to 9 meq/100 ml. The flavor is considered spicy.

*Juice.*—Very juicy at complete maturity

*Brix.*—Generally superior to 13.0 degrees. This characteristic varies slightly with the number of fruit per tree; prevailing cultural practices; and the surrounding climatic conditions.

*Flesh color.*—Yellow flesh (RHS Yellow 13 C), with red pigmentation around the stone (RHS Red 53 A).

Stone:

*Type.*—Clingstone.

*Size.*—Considered medium for the variety. The stone size varies significantly depending upon the tree vigor, crop load and prevailing growing conditions.

*Length.*—Approximately 34.0 to 36.0 millimeters.

*Width.*—Approximately 26.0 to 28.0 millimeters.

*Diameter.*—Approximately 22.0 to 23.0 millimeters.
*Form.*—Elliptic.
*Base.*—Straight.

Apex:
*Shape.*—The stone apex has a small prominent tip.
*Stone cavity.*—Considered medium size, with an elliptic-form and dimensions corresponding to the stone's dimensions.

Stone surface:
*Surface texture.*—The pit is transversely furrowed on its entire surface. Furrows are more pronounced toward the apex. The stone is pitted toward the base. Relief is prominent generally and present basally.
*Ridges.*—The surface texture is generally characterized by more prominent ridges along the ventral edges and is more prominent at the apical tip.

Ventral edge:
*Width.*—Considered medium, and having a dimension of approximately 3.0 millimeters at mid-suture.

Dorsal edge:
*Shape.*—Slightly grooved.
*Stone color.*—The color of the dry stone is generally considered an orange to red-brown (RHS Greyed Orange 176 A to RHS Greyed Red 178 A).
*Tendency to split.*—Splitting is absent.

Kernel:
*Size.*—The kernel is considered medium.
*Length.*—About 20.0 millimeters.
*Width.*—About 14.0 millimeters.
*Thickness.*—About 6.0 millimeters.
*Form.*—Considered oblate and elliptic.
*Pellicle.*—Pubescent.
*Color.*—The kernel skin is a light range yellow (RHS Yellow Orange 16 D). The almond is cream-white (RHS Orange White 159 D). The kernel and its embryo are mature at the time of fruit maturity.

Use: The subject variety 'Nectalady' is considered to be a nectarine tree of the very early season of maturity, and which produces fruits that are considered firm, attractively colored. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

Keeping quality: Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. The fruit of the new nectarine variety showed minimal bruising of the flesh or skin damage after being subjected to normal harvesting and packing procedures. Its resistance to handling during harvest and packing and its long shelf life without alteration after harvest easily permit 3 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of nectarine tree as illustrated and described, characterized by fruit of very long shelf life without alteration after harvesting, and with a semi-sweet yellow flesh of high eating quality and an attractive skin, with a very high percentage of red blush.

* * * * *